(12) United States Patent
Fuhr et al.

(10) Patent No.: US 7,596,957 B2
(45) Date of Patent: Oct. 6, 2009

(54) DEVICE AND METHOD FOR HANDLING A PROBE

(75) Inventors: Günter Fuhr, Berlin (DE); Uwe Schön, Neunkirchen (DE); Heiko Zimmermann, Kronberg im Taunus (DE); Young-Joo Oh, Sulzbach (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 629 days.

(21) Appl. No.: 10/564,904

(22) PCT Filed: Jul. 19, 2004

(86) PCT No.: PCT/EP2004/008051

§ 371 (c)(1),
(2), (4) Date: Feb. 21, 2006

(87) PCT Pub. No.: WO2005/010499

PCT Pub. Date: Feb. 3, 2005

(65) Prior Publication Data

US 2006/0156753 A1    Jul. 20, 2006

(30) Foreign Application Priority Data

Jul. 18, 2003   (DE) ................. 103 32 799

(51) Int. Cl.
*F24F 3/16* (2006.01)
(52) U.S. Cl. .......................................... 62/78
(58) Field of Classification Search .............. 62/78, 62/388
See application file for complete search history.

(56) References Cited

U.S. PATENT DOCUMENTS

| | | | |
|---|---|---|---|
| 3,267,830 A | 8/1966 | Gaasbeek | |
| 4,284,894 A | 8/1981 | Sitte et al. | |
| 4,302,950 A * | 12/1981 | Sitte | 62/51.1 |
| 4,566,293 A | 1/1986 | Arner et al. | |
| 4,612,916 A | 9/1986 | Akers et al. | |
| 4,680,945 A | 7/1987 | Hoffmeister | |
| 5,048,300 A | 9/1991 | Lihl | |
| 5,262,578 A | 11/1993 | Hall | |
| 5,352,898 A | 10/1994 | Mehta | |
| 5,644,922 A | 7/1997 | Linden et al. | |
| 5,730,777 A | 3/1998 | Petersen et al. | |
| 2003/0127951 A1 | 7/2003 | Garcia | |

FOREIGN PATENT DOCUMENTS

| | | |
|---|---|---|
| DE | 4012600 A1 | 11/1990 |
| DE | 4030186 A1 | 4/1991 |

(Continued)

OTHER PUBLICATIONS

PCT/EP2004/008051 Search Report.

*Primary Examiner*—Melvin Jones
(74) *Attorney, Agent, or Firm*—Caesar, Rivise, Bernstein, Cohen & Pokotilow, Ltd.

(57) ABSTRACT

The invention relates to a device and method for handling a probe, in particular, for treating, examining, inserting or extracting a cryoprobe. According to the invention, said probe is surrounded by an ambient gas, during handling, and an air-conditioning device (33) cools, dries and/or at least partially replaces the ambient gas by a protective gas, in order to prevent deterioration of the probe by the ambient gas during handling.

28 Claims, 11 Drawing Sheets

FOREIGN PATENT DOCUMENTS

| | | |
|---|---|---|
| DE | 69426116 T2 | 10/2001 |
| EP | 0978682 B1 | 11/2005 |
| FR | 772020 | 10/1934 |
| GB | 2276088 | 9/1994 |
| GB | 2306376 | 5/1997 |
| WO | 0216844 A1 | 2/2002 |

* cited by examiner

DEVICE AND METHOD FOR HANDLING A PROBE

BACKGROUND OF THE INVENTION

The invention relates to a device and a method for handling a sample, in particular for treating, examining or inserting or extracting a cryosample.

The freezing of samples of biological material while maintaining the vitality of the sample material at temperatures of liquid nitrogen is known in the areas of biology, pharmacology, medicine and biotechnology. Such samples are also designated as cryosamples and are customarily stored and transferred in sample containers, the sample containers being placed in so-called cryotanks with liquid nitrogen for freezing the samples. However, during the inserting of the sample containers into the cryotanks and during the subsequent removal of the sample containers from the cryotanks various problems occur that are briefly described in the following.

For the one, the cryotanks must be opened with the cryosamples located in them for inserting and extracting the sample container, during which moisture can fall into the cryotank from the air surrounding the cryotank, which leads to an ice formation in the cryotank.

For the other, the sample containers removed from the cryotank come in contact with the relatively warm and moist air surrounding the cryotank during their removal from the cryotank, which leads to condensations and subsequent ice formations on the removed sample containers. This ice formation is undesired since it renders the identification of the sample container and the automating of the handling processes difficult and requires a thawing, rubbing off or some other removal of the frost or ice cover formed on the sample container. In addition, the ice formation on the sample containers can also render electrical contacts on the sample containers inaccessible and freeze movable mechanical devices on the sample containers.

In addition, the contact of the cryosamples with the germ-containing ambient air can result in a germination, which is also undesired.

However, the problems previously described occur not only during the insertion and extraction of sample containers in cryotanks but also during other handling or treating of sample containers with cryosamples when they come in contact with the ambient air.

SUMMARY OF THE INVENTION

The invention is therefore based on the task of creating a method and a device for handling cryosamples in which the falling in of moisture into the cryotank is avoided, undesired ice formations on the cryosamples and on the sample containers for the cryosamples is prevented and/or no germination of the cryosamples takes place.

The invention comprises the general technical teaching of preventing a contact with the surrounding, relatively moist, usually germ-containing air when handling samples and/or sample containers, in order that no ice formation can occur on the samples and/or sample containers and that the samples are not germinated.

Within the scope of this general concept of the invention the ice formation on the sample containers and/or samples and their germination can be prevented in various ways as is explained in the following.

One possibility for this is to surround the samples and/or sample containers with a protective gas during handling in order to prevent a direct contact with the relatively moist ambient air. The protective gas is preferably a gaseous nitrogen that is used in any case for cooling the cryosamples and can therefore be used without great additional expense even as protective gas for the samples and/or sample containers. However, the invention is not limited to nitrogen as regards the protective gas to be used but can basically also be realized with other protective gases that prevent an ice formation on the samples and/or sample containers.

Another possibility for preventing an ice formation on the samples and/or sample containers is to cool the ambient gas surrounding the samples and/or sample containers in order to reduce the temperature gradient between the ambient gas and the surface of the samples and/or sample containers and thus counteract condensations on the samples and/or sample containers.

Furthermore, there is the possibility of drying the ambient gas surrounding the samples and/or sample containers in order to prevent an ice formation on the samples and/or sample containers.

However, the previously described techniques for preventing an ice formation are not mutually exclusive but rather can be used with each other in any desired combination.

The protective gas can thus fulfill various functions within the framework of the invention namely, the cooling, drying and protection against germination.

In order to dry, cool and/or exchange the ambient gas surrounding the sample and/or sample container, the device of the invention preferably has a climate control equipment. This concept of climate control equipment used in the framework of the invention is to be understood in a general manner. For example, the function of the climate control equipment can also be fulfilled by liquid nitrogen that is contained in a cryotank serving to store the samples and at least partially replaces the ambient gas of the sample and sample container, thus protecting the sample and sample container. In this instance, the climate control equipment consists of structural components that make possible an outgassing of the liquid nitrogen from the cryotank into the surroundings of the sample and/or sample container.

In a preferred embodiment of the invention a protective container is provided that receives the sample and/or sample container during the handling, the climate control equipment being connected to the protective container in order to dry and cool the ambient gas present in the protective container and/or replace it with the protective gas. Therefore, an artificial atmosphere is preferably created in the protective container in this instance that prevents an ice formation on the sample and/or sample container.

The protective container can be designed, e.g., as a protective bell or protective hood, the protective hood or protective bell preferably having an opening on its bottom for introducing or removing the sample and/or sample container. Such a protective hood or protective bell can be placed on the sample and/or sample container in order to protect it during a subsequent handling. However, it is also possible that the protective hood or protective bell is placed on a cryotank so that the removal opening of the cryotank is located within the protective hood or protective bell and is therefore also protected.

In a variant of the invention the protective hood or protective bell is man-accessible (walkable) so that an operator can perform the handling of the sample and/or sample container within the protective hood or protective bell.

It is advantageous in such a man-accessible protective container if the device in accordance with the invention has a breathing air supply for the operator in the protective container, wherein the breathing air supply can consist in the simplest case of a breathing-air hose that connects the operator to the outside of the protective container.

On the other hand, in another variant of the invention the protective container is portable so that an ice formation can be prevented even during the transport of a sample and/or sample container.

The previously cited climate control equipment for the protective container preferably has a protective gas source in order to fill the protective container at least partially with the protective gas, the protective gas preventing a deterioration of the sample during its handling. Such a protective gas source can have, e.g., an at least partially open protective-gas storage container in which the protective gas is present in liquefied form, the liquefied protective gas outgassing into the protective container. For example, liquid nitrogen can be present in the protective-gas storage container that outgases on account of the surrounding warmth into the protective container.

Furthermore, a heating element can be provided, which heats the liquefied protective gas present in the protective-gas storage container and thus furthers and accelerates the outgassing. Such a heating element can consist, e.g., of a current heater; however, other construction types of the heating element are also possible.

Furthermore, the protective-gas storage container can have a filter element in order to retain bacteria, viruses and other particles during the outgassing of the protective gas that are present in the liquefied protective gas.

It is furthermore advantageous if the protective container has an at least partially transparent container wall in order to make a visual monitoring possible during the handling of the sample. This can be achieved, e.g., in that the container wall consists completely of glass or of a transparent plastic; however, it is also possible that only individual inspection windows are positioned in the otherwise nontransparent container wall.

Furthermore, an outlet opening is preferably arranged on the top of the protective container via which excess protective gas can be discharged.

It is appropriate in this instance if a discharge tube is connected to the outlet opening on the outside of the protective container, which tube has a downwardly directed mouth located outside of the protective container. This alignment of the mouth of the discharge tube advantageously prevents air from being able to fall into the protective container from the outside.

Furthermore, in a preferred embodiment of the invention the protective container comprises a gas-tight or gas-exchange-reduced intervention zone in order that the sample and/or sample container in the protective container can be handled from the outside by an operator.

Moreover, the device in accordance with the invention can have a gas-tight or gas-exchange reduced lock in order to be able to introduce and remove the sample and/or sample container or other pieces into and out of the protective container.

In a variant of the invention this lock consists of at least one opening in the protective container and of a flexible curtain covering the opening.

Such a design of the lock offers on the one hand the advantage that no separate operating step is required to open and close the lock.

On the other hand, this design of the lock makes possible a quasi-continuous introduction and removal of pieces, which is important, e.g., in an automatic operation on a belt conveyor road during which cryosamples are pushed from workplace to workplace.

The cold protective gas in the protective container results as a rule in a corresponding cooling off of the container wall, which can lead to condensations caused by cold an its outer side.

In a variant of the invention, the protective container therefore has a heatable container wall in order to prevent such condensations caused by cold on the outer side of the container wall. The heating of the container wall can take place, e.g., by blowing but other heating methods for heating the container wall can also be used.

In another variant of the invention the container wall is, however, thermally insulated in order to reduce the condensation caused by cold on the outside of the container wall. For example, the container wall can be manufactured to this end from Plexiglas, the wall thickness being preferably in a range from 8 to 15 mm in order to achieve a sufficient insulating effect.

Furthermore, a UV lamp can be arranged in the protective container in order to sterilize the inner space of the protective container.

In addition, there is also the possibility of arranging a camera in the protective container in order to monitor the sample and/or sample container.

Furthermore, it should also be mentioned that the initially mentioned general concept can also be realized without a protective container. For example, a protective gas can be blown on the sample and/or sample container in order to displace the relatively moist ambient air otherwise present in the surroundings of the sample and/or sample container. In addition, the sample and/or sample container can also be surrounded by a curtain of protective gas generated by suitable blowing jets.

A further variant of a cooling equipment in accordance with the invention is at first described in a general manner in the following.

This cooling equipment in accordance with the invention has a cooling space for receiving cooled material, which cooling space is limited by an inner wall and an outer wall, an intermediate space being present between the inner wall and the outer wall into which space a cooling agent supply line empties. The cooling agent (e.g., liquid nitrogen) is therefore not introduced directly into the cooling space but rather into the intermediate space between the inner wall and the outer wall of the cooling space, the inner wall being permeable for the cooling agent so that the cooling agent enters through the intermediate space between the outer wall and the inner wall through the inner wall into the cooling space.

A buffer material is preferably arranged in the intermediate space between the inner wall and the outer wall of the cooling space which temporarily receives the cooling agent introduced into the intermediate space and delivers it continuously through the inner wall into the cooling space.

The buffer material is therefore preferably porous in order to be able to intermediately store, e.g., liquid nitrogen.

In contrast to the inner wall of the cooling space, the outer wall of the cooling space is preferably non-permeable for the cooling agent in order to prevent an exiting of the cooling agent outward into the surroundings. Furthermore, the outer wall is preferably thermally insulating in order to avoid a cooling off of the surroundings and/or a heating of the cooling equipment.

However, the inner wall of the cooling space preferably consists of a thermally conductive material such as, e.g., metal in order to improve the transfer of heat from the inner cooling space onto the cooling agent located in the intermediate space. Moreover, it is advantageous if the material of the inner wall not only has a good thermal conductivity but also a high specific thermal capacity so that the inner wall with its thermal capacity counteracts undesired fluctuations of temperature as a thermal buffer.

In a preferred embodiment of the invention the inner wall is substantially lattice-shaped so that cooling agent present in the intermediate space can outgas substantially unhindered into the cooling space.

Furthermore, in a preferred embodiment of the invention the cooling space is vat-shaped and has a circumferential edge on its upper surface, the cooling agent feed line preferably having a cooling agent distributor that extends along the circumferential edge of the cooling space and introduces the cooling agent distributed over its length into the intermediate space between the inner wall and the outer wall of the cooling space. Therefore, the cooling agent is introduced uniformly here into the intermediate space between the inner wall and the outer wall of the cooling space, which advantageously results in a uniform temperature distribution in the cooling space since the cooling space is uniformly cooled from all sides.

Moreover, there is the possibility within the framework of the invention that a heating element is arranged in the cooling space in order to heat the cooling space or to thaw the cooled material present in the cooling space. This heating element is preferably arranged under or in a heating plate, the heating plate preferably having several passages that make a circulation of gas possible.

There is the possibility in this instance of placing a removable protective bell on the cooling space in order to avoid the penetration of moisture into the cooling space. This protective bell is preferably at least partially transparent in order to make possible a visual monitoring of the cooled material located in the cooling space.

In a preferred embodiment of the invention the protective bell comprises a sample lock through which the cooled material can be introduced into the cooling space or removed from the cooling space, the sample lock substantially preventing a heat exchange with the surroundings.

Furthermore, a cold gas outlet can be arranged on the bottom of the protective bell and/or on the top of the cooling space via which outlet cooling agent or cold gas can escape from the cooling space. This cold gas outlet produces a large temperature gradient at the level of the cold gas outlet, the temperature above the cold gas outlet being substantially higher than it is below the cold gas outlet. A misting of the protective bell is advantageously prevented in this manner.

Furthermore, a closed loop control of the temperature in the cooling space preferably takes place within the framework of the invention. To this end, the cooling equipment in accordance with the invention preferably has a temperature sensor arranged in the cooling space in order to measure and control the temperature in the cooling space. A controllable cooling agent valve is then preferably provided as an actuator for adjusting the temperature, which valve adjusts the amount of the supplied cooling agent and/or the flow of cooling agent. The actual controlling of the temperature then takes place by a temperature controller that is connected on the input side to the temperature sensor and that controls the cooling agent valve on the output side in accordance with a given temperature target value.

The control of the cooling agent valve can in this instance take place via a pulse generator that alternately opens and closes the cooling agent valve, the opening and closing times of the cooling agent valve being set by the pulse generator and adjusted by the temperature controller. Therefore, the supplying of cooling agent takes place discontinuously here in that the cooling agent valve alternately opens and closes.

The temperature sensor for detecting the temperature in the cooling space is preferably arranged here at the treating position of the cooling space in order to measure and control the optimal treating temperature in the cooling space.

The temperature controller therefore preferably controls the temperature in the cooling space in such a manner that no cooling agent lake forms on the bottom of the cooling space.

It should also be mentioned that the cooling agent is preferably liquid nitrogen. However, the invention is not limited to nitrogen as cooling agent but rather can also be realized with other liquid or gaseous cooling agents that can be introduced into the intermediate space between the inner wall and the outer wall of the cooling space.

The cooling equipment can be used for various temperature ranges such as, e.g., at temperatures of approximately $-150°$ C., $-130°$ C., $-80°$ C., $-40°$ C., $+4°$ C. or $+37°$ C., wherein the previously cited temperature ranges can comprise, e.g., a bandwidth of $\pm 10°$ C., $\pm 5°$ C. or $\pm 2°$ C. A temperature of $37°$ C. is advantageous because the growth temperature of biological cells is then optimal. On the other hand, a temperature of $+4°$ C. offers the advantage that the physiological processes in the cells are delayed. The cell damage (e.g., with Tropsia and DMSO) is less with a manipulation of cells at a temperature less then $4°$ C.

Finally, the invention comprises not only the previously described cooling equipment as apparatus but also the use of such cooling equipment for examining, treating and/or manipulating a cryosample.

BRIEF DESCRIPTION OF SEVERAL VIEWS OF THE DRAWINGS

Other advantageous further developments of the invention are characterized in subclaims or are explained in detail in the following together with the description of the preferred embodiments of the invention using the figures.

DETAILED DESCRIPTION OF THE PREFERRED EMBODIMENTS

Figure 1:
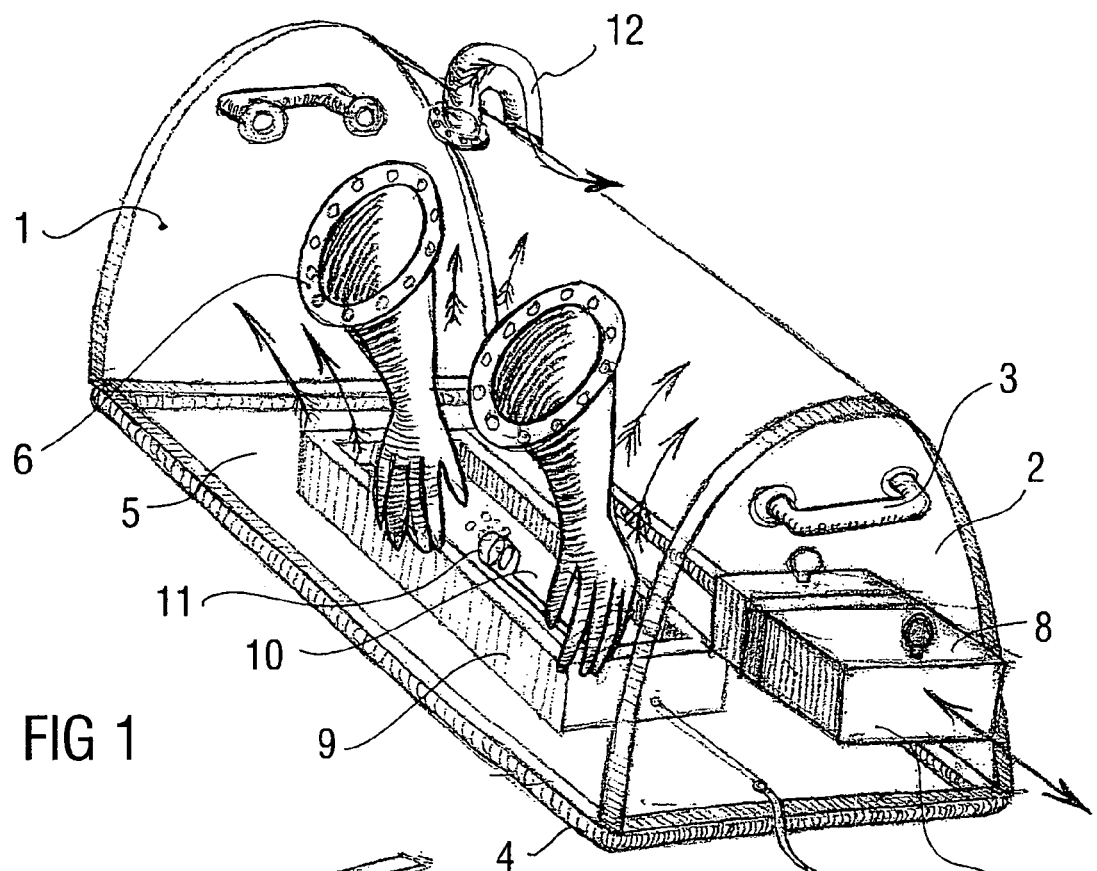
FIG. 1 shows a protective hood in accordance with the invention in a perspective representation.

The cross-sectional view in FIG. 1 shows a protective hood 1 consisting of Plexiglas with a wall thickness of 12 mm and a substantially parabolic cross section, the front sides of the protective hood 1 being closed on both sides by a closure wall 2.

A handle 3 is fastened to each of the closure walls 2 in their upper area so that the protective hood 1 can be raised and moved by an operator.

Furthermore, it should be mentioned that the wall of the protective hood 1 is completely transparent, which makes it possible for the operator to visually monitor the inner space of the protective hood 1.

The protective hood 1 comprises a circumferential seal 4 on its bottom that seals the protective hood 1 after it has been set on a laboratory surface 5.

Furthermore, the protective hood 1 has two intervention zones 6 in the parabolic part of its container wall via which zones the operator standing on the outside can work in the inner space of the protective hood 1.

Moreover, the protective hood 1 has a gas-exchange-reduced lock 7 that is designed as a drawer and is arranged in the closure wall 2 of the protective hood 1. The lock 7 has a cover 8 on its top that can be folded up for introducing or removing a piece out of the protective hood 1.

A vat 9 filled with liquid nitrogen 10 is located as climate control equipment on the laboratory surface 5. After the protective hood 1 has been set on the vat 9, the nitrogen outgassing from the vat 9 fills the inner space of the protective hood 1 and functions as a protective gas, as will be subsequently described in detail.

An electric heating element 11 is arranged in the vat 9 in order to heat the liquid nitrogen 10 located in the vat 9 and to thus accelerate the outgassing of the nitrogen.

Furthermore, an outlet opening is arranged on the top of the protective hood 1 to which an opening discharge tube 12 is connected via which excess nitrogen gas can be conducted out of the inner space of the protective hood 1.

The discharge tube 12 is U-shaped in this instance, the free mouth of the discharge tube 12 being directed downward in order to prevent the falling in of relatively moist ambient air into the inner space of the protective hood 1.

The previously described hood 1 can be placed on a cryosample container (not shown for the sake of simplicity), the outgassing of nitrogen gas from the vat 9 preventing condensations or even ice formations on the cryosample when a cryosample is removed from the cryosample container.

Figure 2:
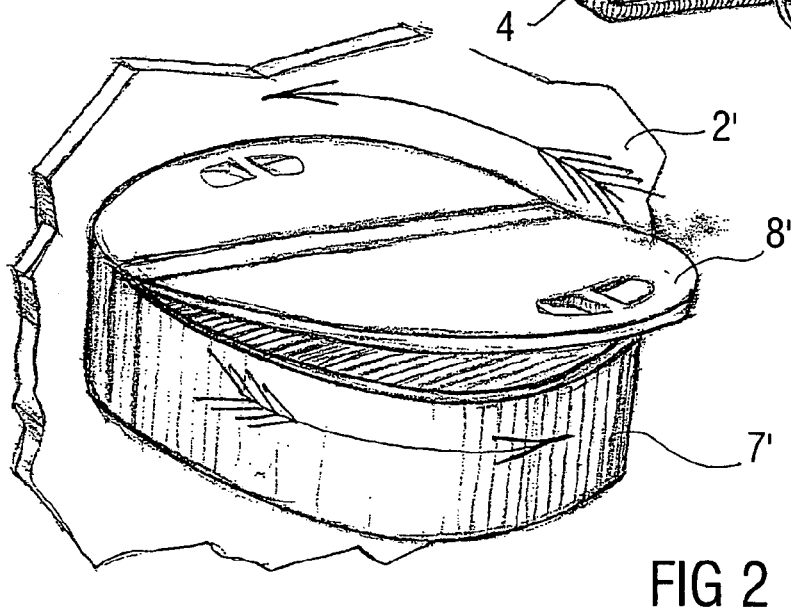
FIG. 2 shows an alternative embodiment of a lock of the protective hood shown in FIG. 1 in a perspective view.

The perspective view in FIG. 2 shows an alternative embodiment of a lock 7' that can be used as instead of the lock 7 shown in FIG. 1. The lock 7' substantially corresponds to the lock 7 shown in FIG. 1 so that the same reference signs are used for corresponding structural components that are characterized, however, for the sake of distinction by an apostrophe.

A particularity of the lock 7' in comparison to the lock 7 is that it is not designed as a movable drawer but rather is rotatably supported in the closure wall 2'.

Figure 3:
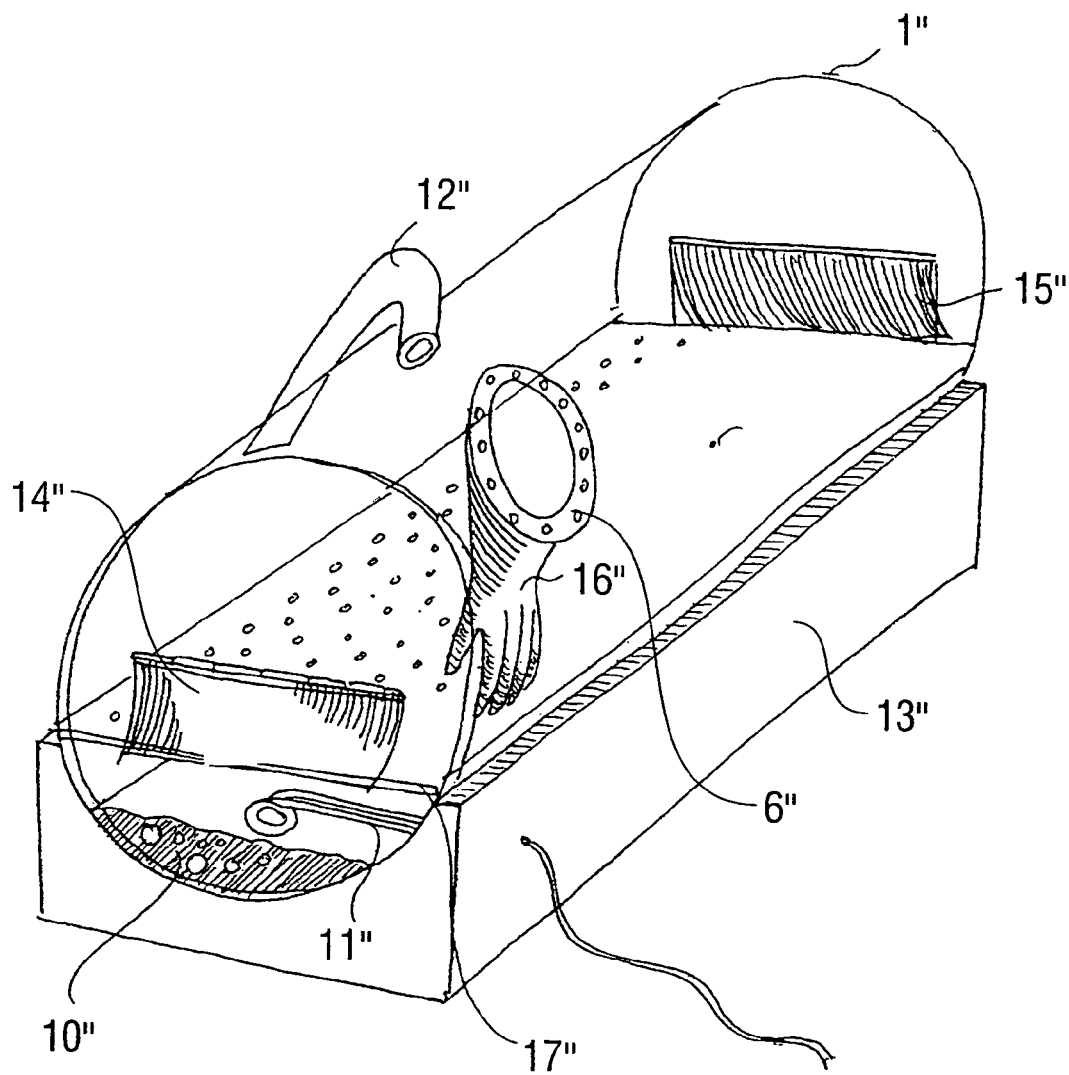
FIG. 3 shows an alternative embodiment of the device in accordance with the invention with a cylindrical protective container.

The embodiment shown in FIG. 3 of a device in accordance with the invention substantially corresponds to the embodiment previously described and shown in FIG. 1, so that in order to avoid repetitions broad reference is made to the previous description for FIG. 1 and the same reference signs are used for corresponding structural components, that are characterized, however, for the sake of distinction by two apostrophes.

A particularity of this embodiment is that a cylindrical protective container 1" is used instead of the parabolic protective hood 1, the protective container 1" being stationarily arranged in the insulating vat 13" that thermally insulates the protective container 1".

Furthermore, the protective container 1" has a lock on both front sides for removing or introducing pieces, the two locks each consisting of an opening in the front side of the protective container 1" and of a flexible curtain 14", 15" that flexibly covers the particular opening and thus prevents the penetration of relatively moist air from the outside into the protective container 1".

Furthermore, only a single intervention zone 6" is shown in the drawing that leads to a rubber glove 16" on the inside of the protective container 1"; however, another intervention zone is additionally provided that is not shown for the sake of simplicity.

Liquefied nitrogen 10" is located in a lower area of the protective container 1" and is heated by a heating element 11" in such a manner that nitrogen gas outgases into the inner space of the protective container 1".

A work platform 17" with holes for the passage of the nitrogen gas outgassing from below is located above the liquefied nitrogen 10".

During operation, cryosample containers containing cryosamples can be introduced into the inner space of the protective container 1" and manipulated inside the protective container 1" without any danger of condensations or ice formations on the cryosample containers.

Figure 4:
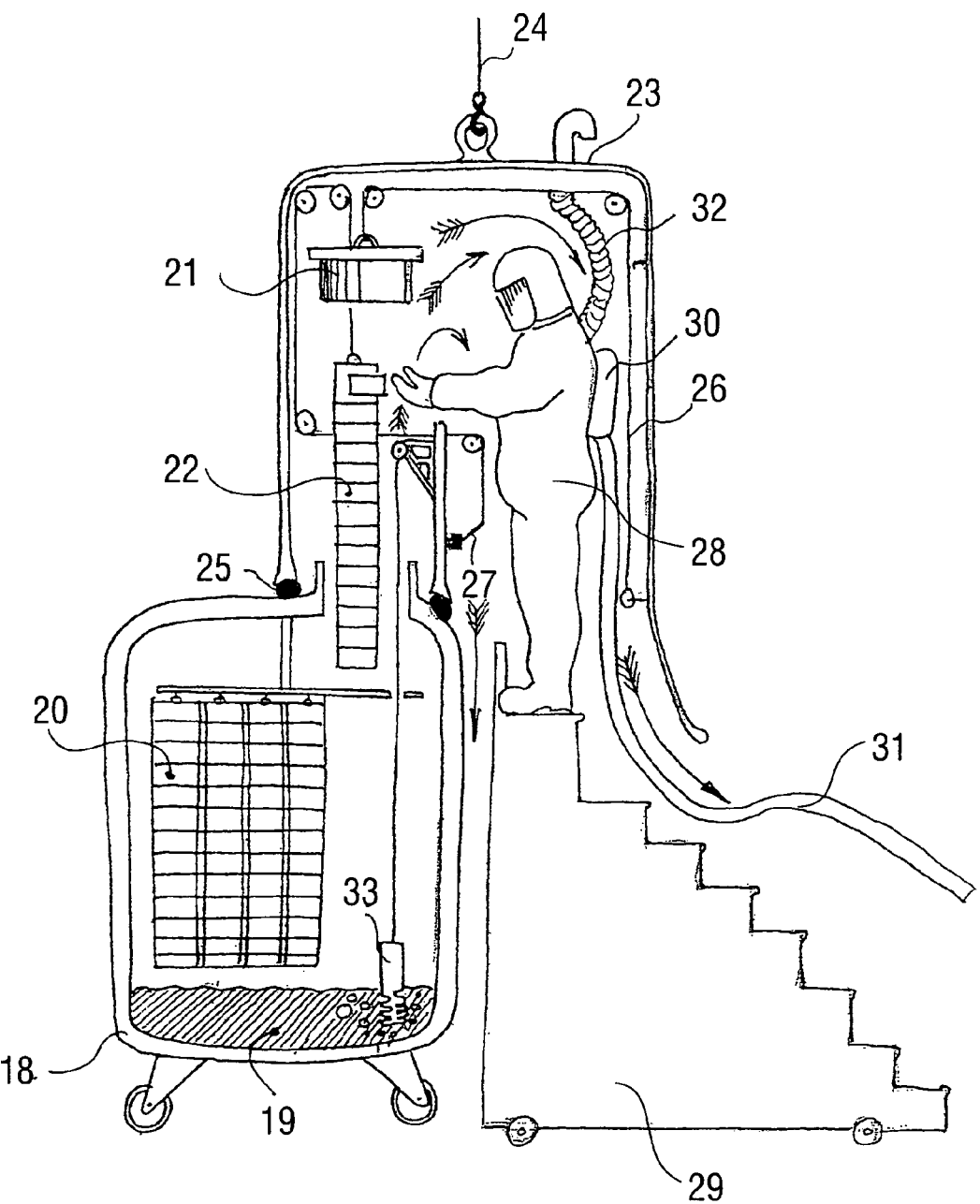
FIG. 4 shows a sectional lateral view of a man-accessible cryotank bell.

The cross-sectional drawing in FIG. 4 at first shows a traditional cryotank 18 in which liquefied nitrogen 19 is located on the bottom.

Several cryosample containers 20 are suspended in the cryotank 18 that are cooled by the liquefied nitrogen 19 and each contain numerous cryosamples.

The cryotank 18 has a tank opening on its top that can be closed by a tank cover 21, the tank cover being shown in the drawings in a raised position in which a cryosample container 22 is being removed through the tank opening of the cryotank 18.

There is customarily the danger during such a removal of the cryosample container 22 that atmospheric moisture from the ambient air falls into the cryotank 18, which results in undesired ice formations in the cryotank 18. Moreover, condensations and subsequent ice formation can occur on the cryosample container 22 during the traditional removal methods, which is also undesired.

In order to prevent these undesired effects, the invention has a cryotank bell 23 that is raised by cable control 24 and can be subsequently placed on the tank opening of the cryotank 18, a 25 sealing the tank opening of the cryotank 18.

The tank cover 21 of the cryotank 18 can then be raised by means of an additional cable control 24 via two deflection rollers in order to free the tank opening of the cryotank 18 for the removal of the cryosample container 22.

The removal of the cryosample container 22 then takes place via another cable control 27 suspended in an appropriate hook on the cryosample container 22.

The operation of the two cable controls 26, 27 and the manipulation of the cryosample container 22 are performed by an operator 28 who can enter into the man-accessible cryotank bell 23 via rollable stairs 29.

Here, the operator 28 wears a protective suit and carries a breathing air supply 30 connected via a line 31 to a supply unit (not shown for the sake of simplicity) arranged outside of the cryotank bell.

As an alternative to the breathing air supply 30, a simple breathing air hose 32 can also be provided that runs out of the cryotank bell 23, the free mouth of the breathing air hose 32 being bent down on the outside of the cryotank bell 23 in order to prevent moist ambient air from falling into the cryotank bell in every instance.

The climate control of the gas volume inside the cryotank bell 23 takes place here by an electrical heating element 33 that is let down by the operator 28 via a cable control into the cryotank 18, so that the heating element 33 heats the liquefied nitrogen 19 and thus accelerates the outgassing of nitrogen gas into the inner space of the cryotank bell 23.

Condensations or even ice formations on the removed cryosample container 22 are prevented by the outgassing nitrogen gas.

In addition, the cryotank bell 23 prevents that moist ambient air falls into the cryotank 18 when the tank cover 21 is opened, which would also result in an undesired ice formation in it.

Figure 5:
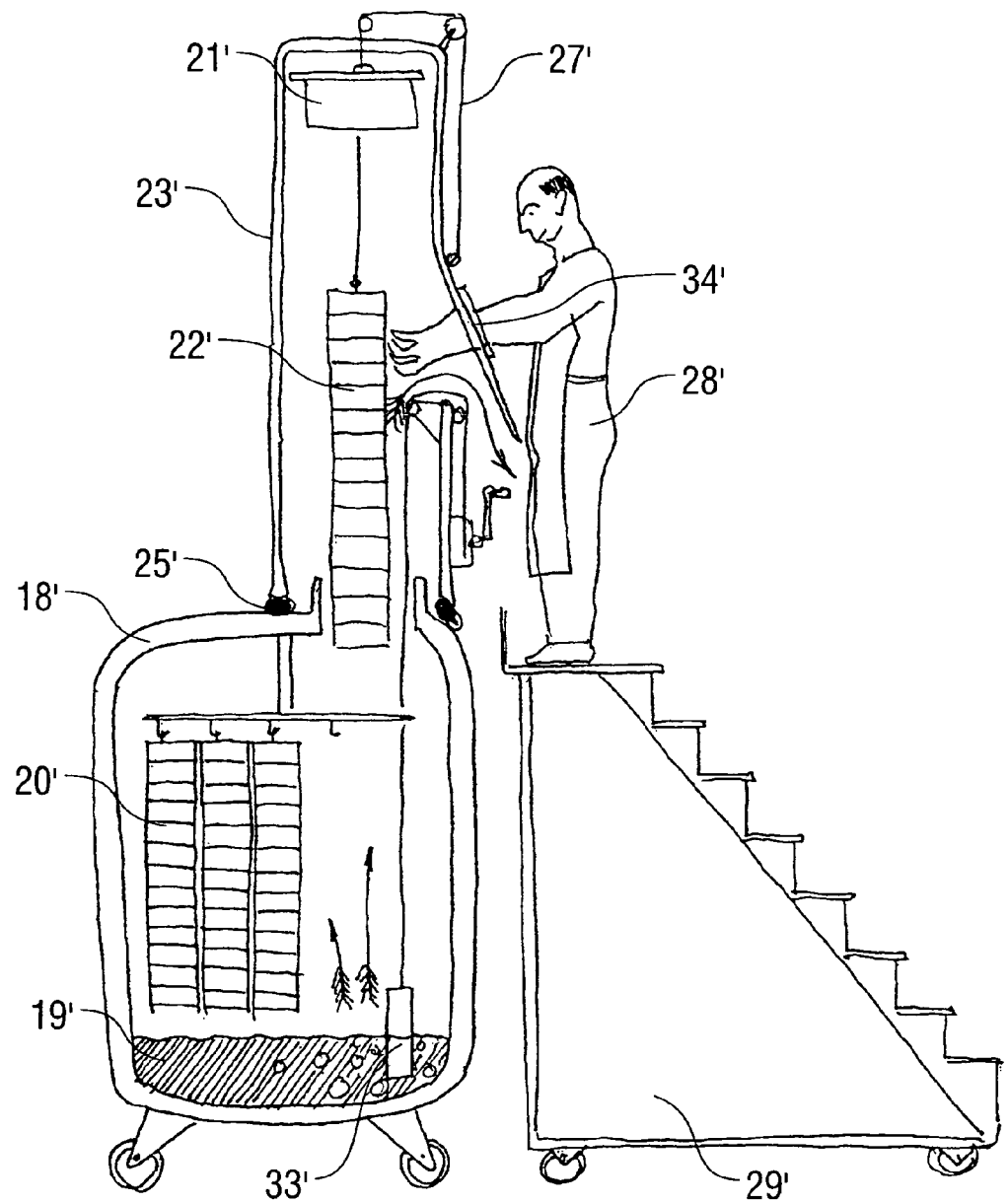
FIG. 5 shows an alternative embodiment of such a cryotank bell.

The embodiment shown in FIG. 5 substantially corresponds to the previously described embodiment represented in FIG. 4 so that in order to avoid repetitions broad reference is made to the previous description and the same reference signs are used for corresponding structural components, which are characterized, however, for the sake of distinction by an apostrophe.

A particularity of this embodiment is that the cryotank bell 23' is not man-accessible.

Instead, the cryotank bell has intervention zones 34' through which the operator 28' can manipulate the cryosample container 22' lifted out of the cryotank 18'.

Figure 6:
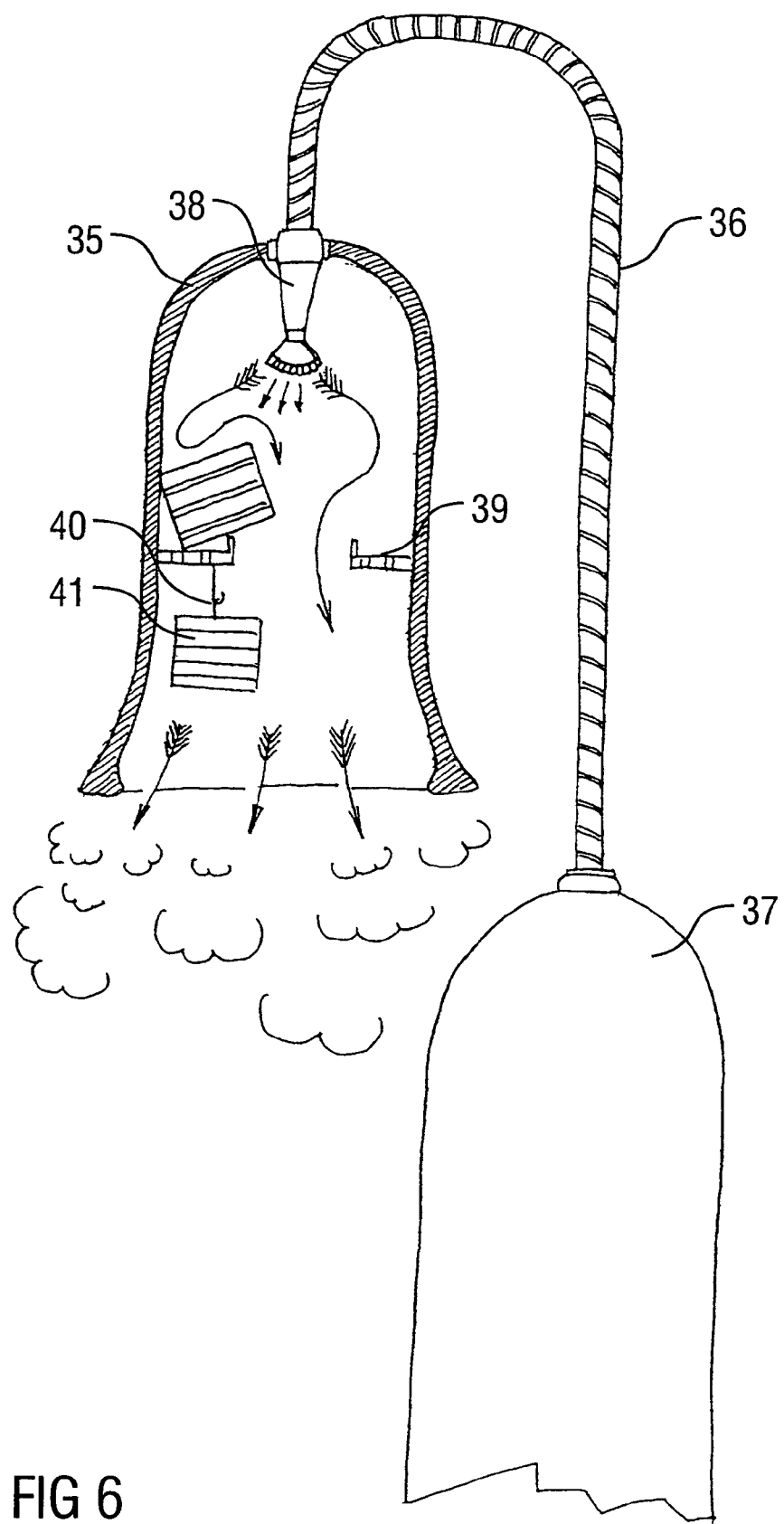
FIG. 6 shows a simple embodiment of a portable protective bell in a lateral view.

The embodiment of a device in accordance with the invention and shown in FIG. 6 consists substantially of a protective bell 35 connected via a gas line 36 to a container for compressed nitrogen gas 37, the gas line 36 emptying in the protective bell 35 into a nozzle arrangement 38 through which nitrogen is delivered into the inner space of the protective bell 35.

Shelves 39 and suspension devices 40 for holding cryosample containers 41 are located in the protective bell 35. The cryosample containers 41 are arranged here inside the protective bell 35 and are therefore protected by the nitrogen gas flowing out from the nozzle arrangement 38, whereby a condensation or even an ice formation on the cryosample containers 41 is prevented.

Figure 7:
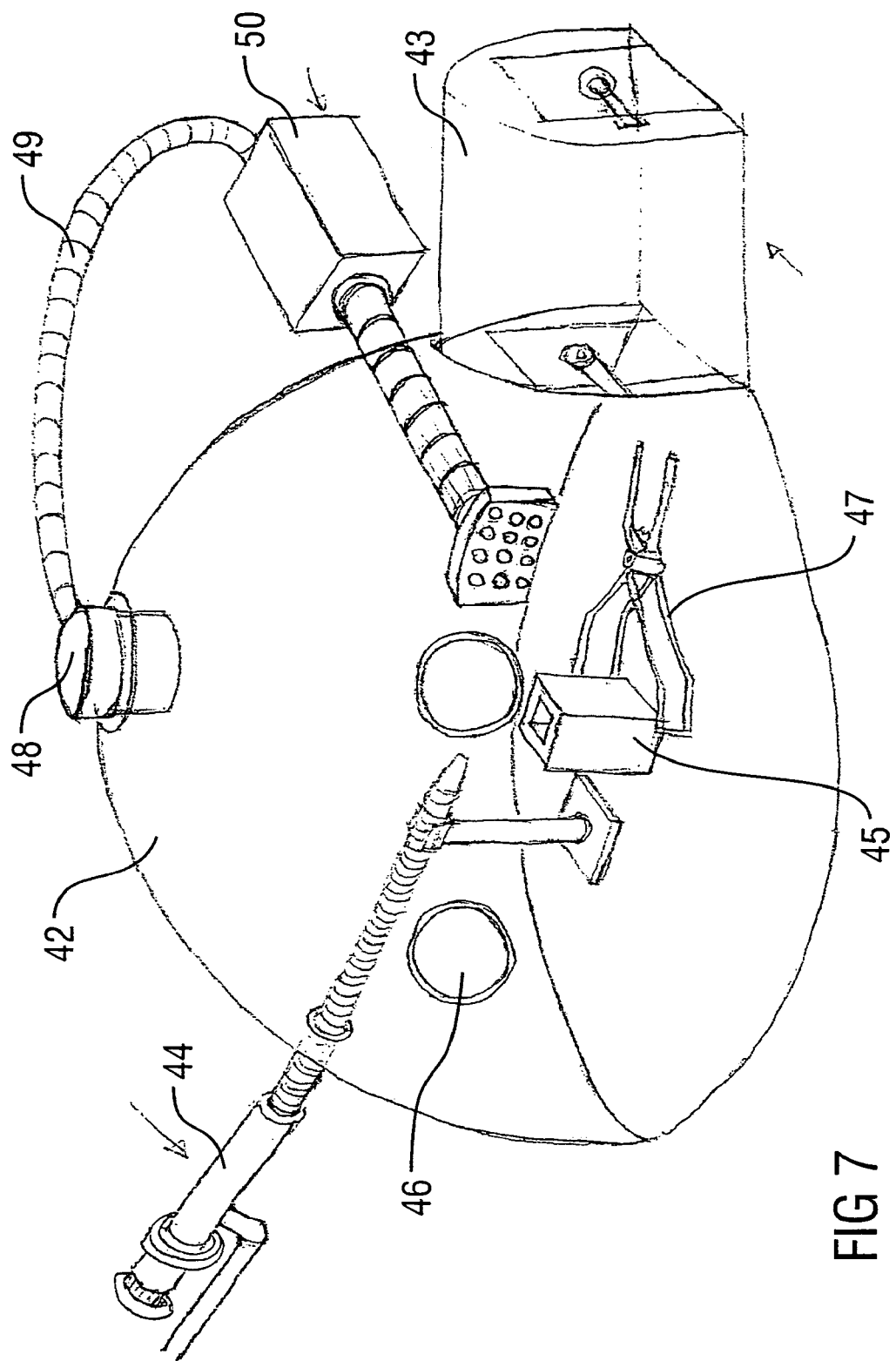
FIG. 7 shows a perspective view of an alternative embodiment of the device in accordance with the invention.
Figure 8:
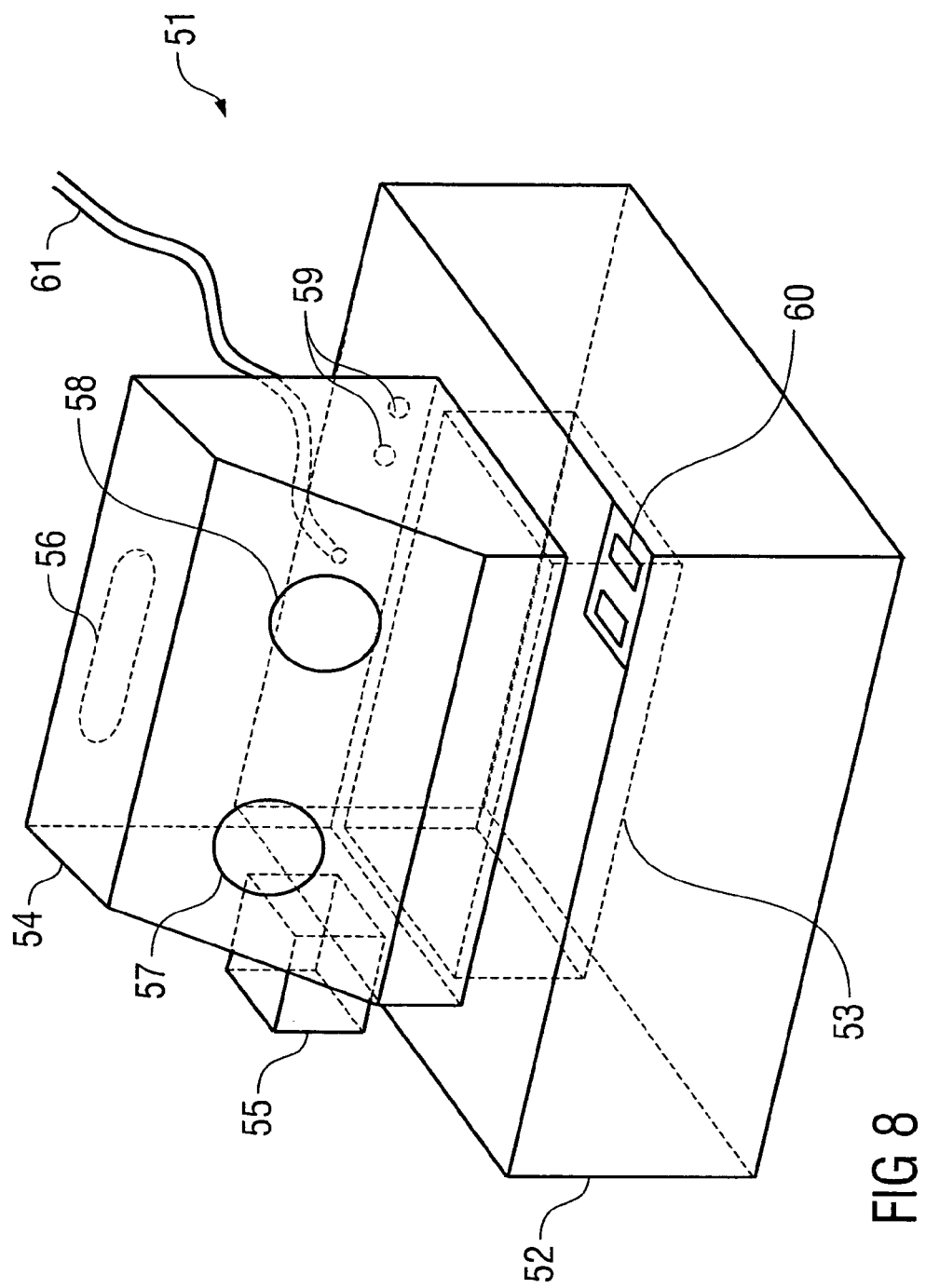
FIG. 8 shows a perspective view of a preferred embodiment of the cooling equipment in accordance with the invention with a protective bell placed on the equipment.
Figure 9:
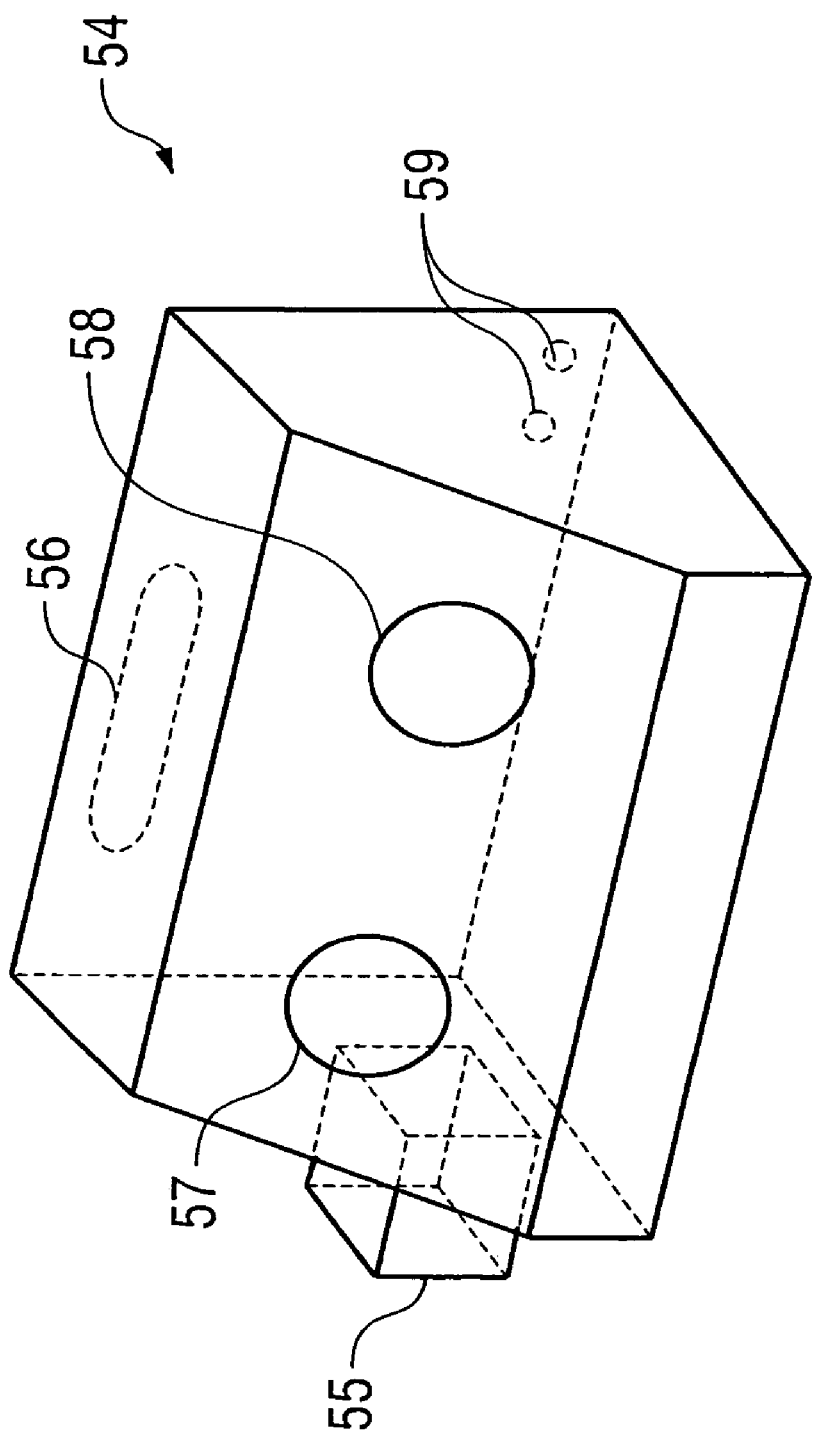
FIG. 9 shows a perspective view of the protective bell of FIG. 8 in the removed state.
Figure 10:
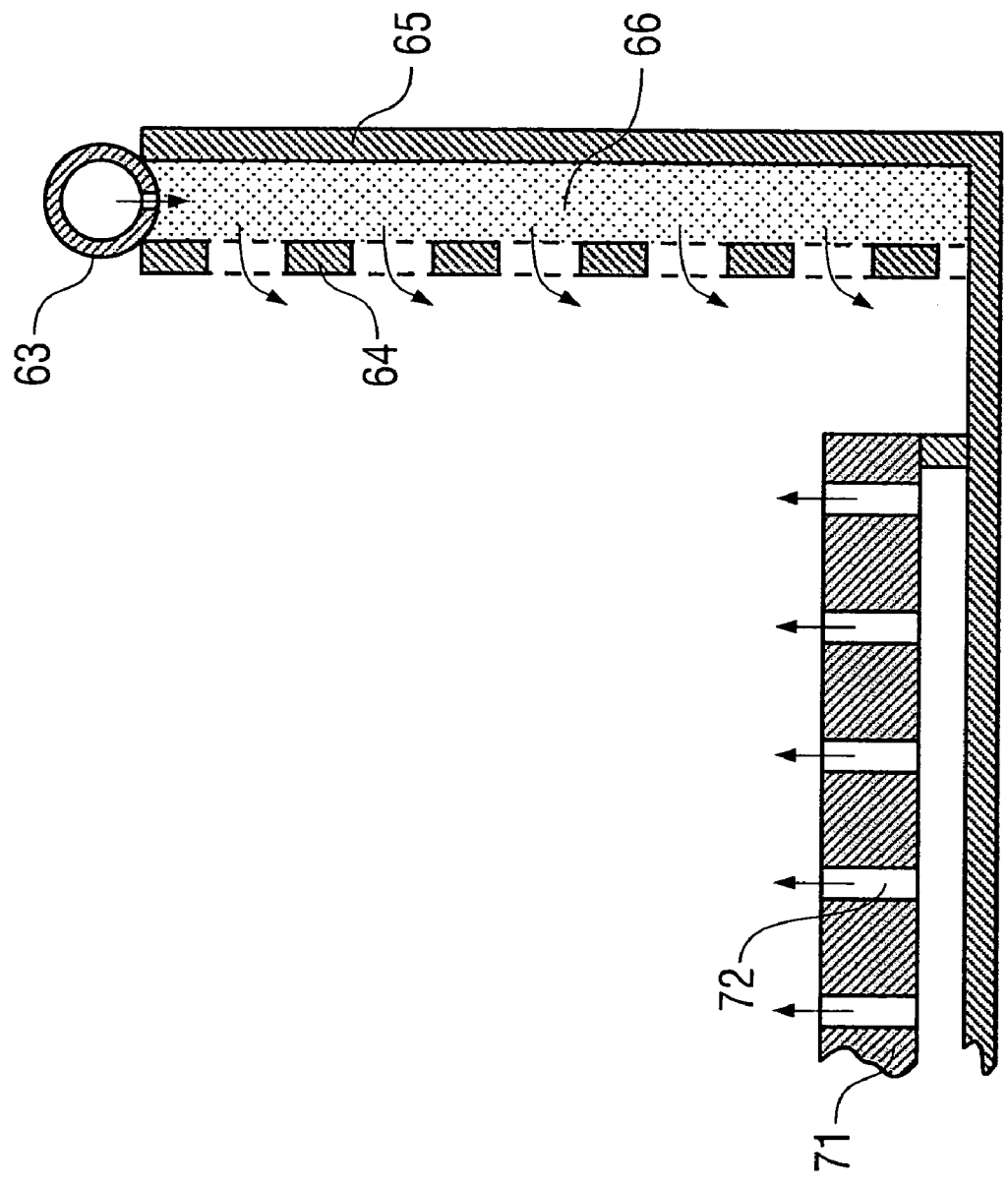
FIG. 10 shows a cross-sectional view of the wall structure of the cooling space in the cooling equipment of FIG. 8.
Figure 11:
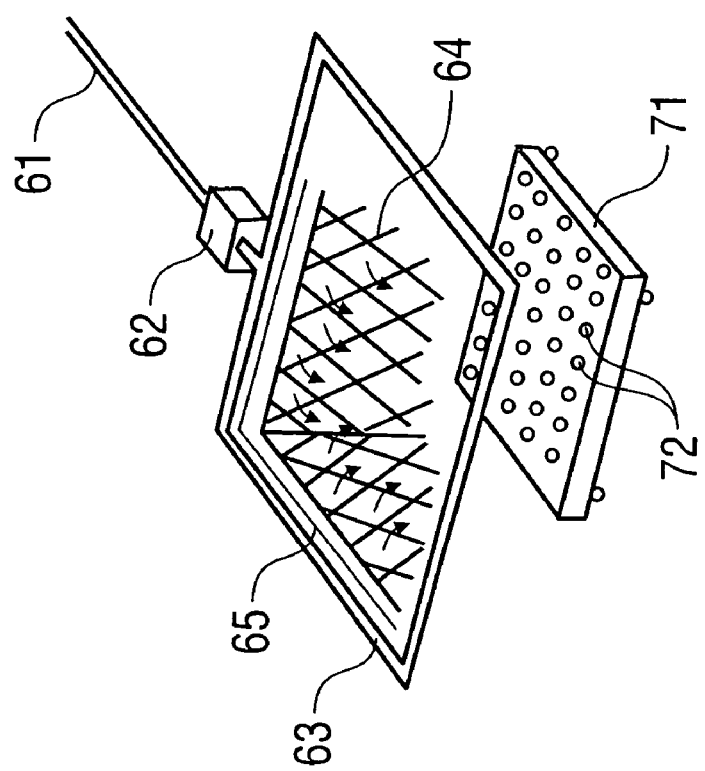
FIG. 11 shows a simplified perspective representation of the cooling agent supply in the cooling equipment of FIG. 8.
Figure 12:
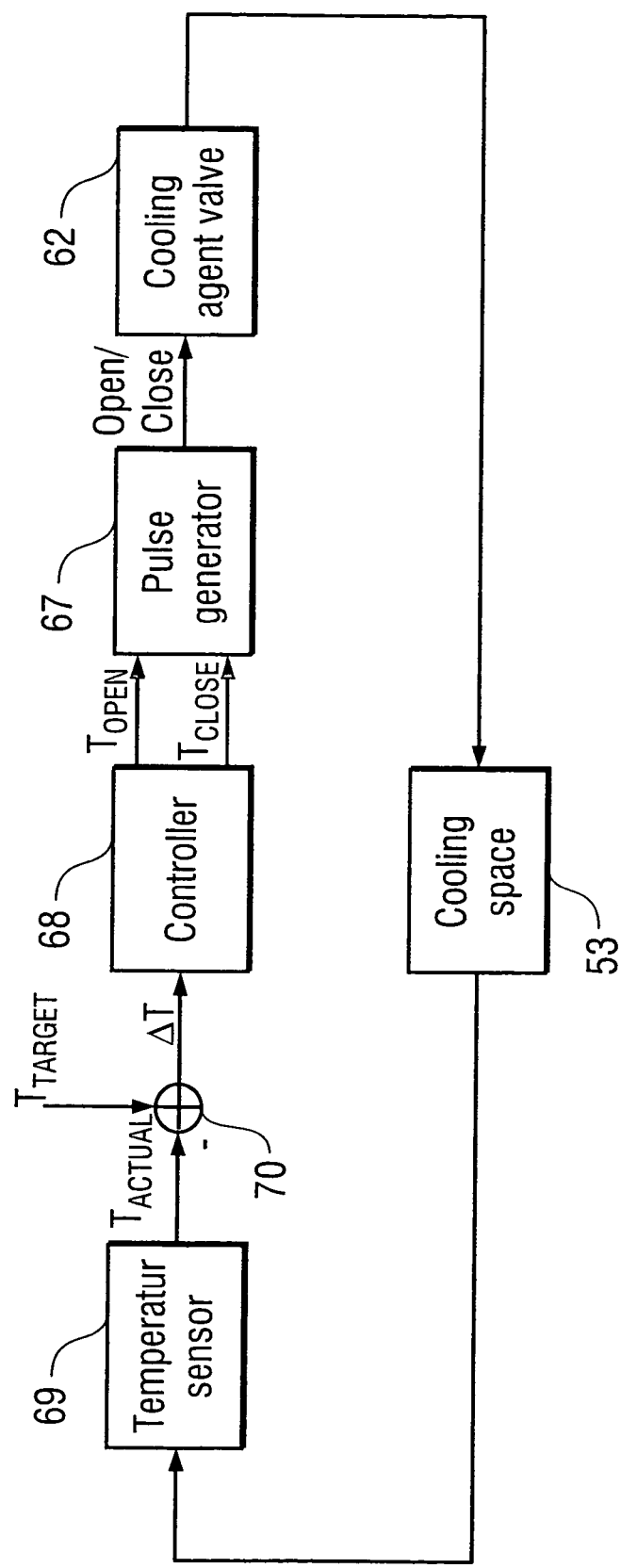
FIG. 12 shows a control-engineering equivalent circuit diagram of the cooling apparatus of FIG. 8.

Finally, FIG. 7 shows another embodiment of the invention with a protective container 42 into which cryosamples or other pieces can be introduced or removed via a lock 43.

Nitrogen gas is introduced via a gas feed line 44 into the protective container 42 where it is directed against a cryosample container 45.

In this instance, the cryosample container 45 can be manipulated from the outside through two intervention zones 46 by an operator for which, e.g., tongs 47 can be used.

A controllable valve 48 is located on the top of the protective container 42 and makes possible a removal of the relatively moist air in the protective container 42 at the beginning as long as the protective container 42 has not yet been completely filled with nitrogen gas.

Subsequently, the valve 48 conducts the nitrogen gas exiting at the top via a hose 49 to an air-circulation plant 50 that introduces the nitrogen gas removed via the valve 48 back into the protective container 42.

In this embodiment the nitrogen gas surrounding the cryosample container 45 also prevents a condensation or even an ice formation on the cryosample container 45.

The embodiment shown in FIGS. 8-12 of a cooling equipment 51 in accordance with the invention serves to temper a cooling space for receiving cryosamples during an examination, manipulation and/or treating.

To this end, the cooling equipment 51 has a cryovat 52 with a vat-shaped cooling space 53 open at the top, a removable protective bell 54 being placed on the cryovat 52, which prevents moisture from penetrating out of the surroundings into the cooling space and is shown in detail in FIG. 2.

The protective bell 54 has a sample lock 55 for introducing cryosamples into the cooling space 53 and for removing cryosamples from the cooling space 53. This lock is attached to the side of the protective bell 54 and substantially prevents a heat exchange with the surroundings and minimizes the moisture in the cooling space 53 during the introduction of cryosamples and during the removal of cryosamples.

Furthermore, the protective bell 54 has a lamp 56 on its top in order to illuminate the cooling space 53 and thus facilitate the manipulation of the cryosamples in the cooling space 53.

The protective bell 54 itself consists of a transparent material, which permits a simple visual monitoring by an operator.

Two traditional glove sleeves 57, 58 through which an operator can manipulate the cryosamples in the cooling space 53 without a gas exchange are located on the slanting front side of the protective bell 54.

Furthermore, two openings 59 via which cold gas can escape from the protective bell 54 are located on the back side of the protective bell 54. The two openings 59 have the consequence that a large temperature gradient is obtained at the level of the two openings 59 since cold gas escapes to the outside from the two openings 59. The atmosphere in the protective bell 54 above the openings 59 is therefore substantially warmer then below the openings 59, which counteracts a misting of the inner walls of the protective bell 54.

Furthermore, a control and display panel 60 is located on the front side of the top of the cryovat 52 on which the temperature in the cooling space 53 can be displayed and adjusted.

The cooling of the cooling space 53 takes place here by liquid nitrogen supplied from a nitrogen tank (e.g., an Apollo container) via a nitrogen line 61, the nitrogen line 61 not emptying directly into the cooling space 53 in order to avoid the formation of a nitrogen lake on the bottom of the cooling space 53. Instead, the nitrogen line 61 empties via an electrically controllable cooling agent valve 62 into a cooling agent supply line 63, the cooling agent supply line 62 extending along the circumferential edge of the vat-shaped cooling space 53 and releases liquid nitrogen over its length in a distributed manner.

The cooling space 53 is limited here by a metallic, lattice-shaped inner wall 64 surrounded by an outer wall 65, the inner wall 64 and the outer wall 65 enclosing an intermediate space in which a buffer material 66 is arranged. The cooling agent supply line 63 is arranged in a lateral direction between the inner wall 64 and the outer wall 65 above the buffer material 66 and has downwardly directed outlet openings through which liquid nitrogen is delivered out of the interior of the cooling agent supply line 63 into the buffer material 66. The buffer material 66 absorbs the liquid nitrogen and delivers it continuously through the lattice-shaped inner wall 64 into the cooling space 53.

The cooling agent valve 62 operates discontinuously here in that it either opens or closes.

The control of the cooling agent valve 62 takes place here by a pulse generator 67, the opening time $T_{OPEN}$ and closing time $T_{CLOSE}$ are given for the cooling agent valve 62 by a controller 68 in order to dose the cooling agent.

The controlling takes place here as a function of the temperature in the cooling space 3, which is measured by a temperature sensor 69, the temperature sensor 69 being arranged on the treating position of the cooling space 53.

The temperature sensor 69 therefore measures a temperature $T_{ACTUAL}$ and transmits it to a subtractor 70 that obtains a target value $T_{TARGET}$ for the temperature in the cooling space 53 as another input variable and calculates a target-actual deviation ΔT.

The controller 68 then adjusts the opening time $T_{OPEN}$ and the closing time $T_{CLOSE}$ for the cooling agent valve 62 in such a manner that the desired temperature (e.g., −630° C.) prevails in the cooling space 53 without a nitrogen lake forming on the bottom of the cooling space 53.

Furthermore, a heating plate 71 is arranged on the bottom of the cooling space 53 that makes possible a heating of the cryosample and of the cooling space 53.

Numerous vertical continuous passages 72 are arranged in the heating plate 71 that make a circulation of gas possible.

The invention is not limited to the previously described preferred embodiments but rather a plurality of variants and modifications are possible that also make use of the concept of the invention and therefore fall within its protective scope.

The invention claimed is:

1. A device for handling a sample, the sample being a cryosample surrounded during the handling by an ambient gas, comprising:
   a) climate control equipment adapted to perform an operation selected from the group consisting of:
      i. cooling the ambient gas,
      ii. drying the ambient gas, and
      iii. replacing the ambient gas with a protective gas in order to avoid deterioration of the sample by the ambient gas,
   b) a protective container for receiving the sample during the handling, the climate control equipment being connected to the protective container in order to perform said operation, and
   c) a protective gas source that is part of the climate control equipment and is adapted to fill the protective container at least partially with the protective gas, the protective gas preventing a deterioration of the sample during its handling,
wherein the protective gas source comprises an at least partially open protective-gas storage container inside the protective container, said protective-gas storage container containing liquefied protective gas adapted to outgas into the protective container.

2. The device according to claim 1, wherein a heating element is provided for heating the liquefied protective gas present in the protective-gas storage container and for furthering the outgas sing of the protective gas.

3. The device according to claim 1, wherein the protective-gas storage container has a filter element in order to retain substances selected from the group consisting of:
   a) bacteria,
   b) viruses, and
   c) other particles present in the liquefied protective gas during outgassing.

4. The device according to claim 1, wherein the protective container is mobile and has an opening on its bottom in order to introduce the sample into and to remove it from the protective container.

5. The device according to claim 4, further comprising a seal for sealing the opening of the protective container after the protective container has been placed on the sample.

6. The device according to claim 1, wherein the protective container has an at least partially transparent container wall in order to make visual monitoring possible during the handling of the sample.

7. The device according to claim 1, wherein an outlet opening is arranged on top of the protective container for discharging excess ambient gas.

8. The device according to claim 7, wherein a discharge tube is connected to the outlet opening on the outside of the protective container, said discharge tube having a downwardly directed mouth located outside of the protective container.

9. The device according claim 1, wherein the protective container has at least one gas-tight intervention zone adapted to enable treating the sample in the protective container.

10. The device according to claim 1, further comprising a gas-tight lock adapted to enable introducing the sample into the protective container and removing the sample from the protective container.

11. The device according to claim 10, wherein the lock comprises an opening in the protective container and a flexible curtain covering the opening.

12. The device according to claim 10, wherein a lock is arranged on each of opposite sides of the protective container in order to make automated operation possible.

13. The device according to claim 1, wherein the protective container has a thermally insulating container wall adapted to prevent condensation caused by cold on an outside surface of the device.

14. The device according to claim 1, wherein the protective container has a heatable container wall adapted to prevent condensation caused by cold on an outside surface of the device.

15. The device according to claim 1, wherein at least one UV lamp for sterilization is mounted in the protective container.

16. The device according to claim 1, wherein the protective container is portable and is bell-shaped or hood-shaped.

17. The device according to claim 1, wherein the protective container is man-accessible.

18. The device according to claim 17, further comprising a breathing air supply for an operator in the protective container.

19. The device according to claim 1, wherein the protective gas is substantially sterile.

20. A method for handling a sample, the sample being a cryosubstrate surrounded during the handling by an ambient gas, comprising the following steps:
   a) introducing the sample into a protective container,
   b) performing an operation selected from the group consisting of:
      i. cooling the ambient gas,
      ii. drying the ambient gas, and
      iii. replacing the ambient gas with a protective gas in order to avoid a deterioration of the sample by the ambient gas, and
   c) using a protective gas source in order to fill the protective container at least partially with the protective gas that prevents a deterioration of the sample during its handling,
wherein liquefied protective gas outgasses into the protective container from an at least partially open protective-gas storage container of the protective gas source, said protective-gas storage container being provided inside the protective container.

21. The method according to claim 20 wherein the sample is first arranged in a sample container and is not removed from the sample container until in the protective container.

22. The method according to claim 20, wherein the protective container is filled at least partially with the protective gas prior to removing the sample from the sample container.

23. The method according to claim 20, wherein liquefied protective gas is heated in order to further the outgassing of the protective gas.

24. The method according to claim 20, wherein the protective gas is filtered prior to the filling of the protective container in order to retain substances selected from the group consisting of:
   a) bacteria,
   b) viruses, and
   c) other particles present in the liquefied protective gas during outgassing.

25. The method according to claim 20, wherein the protective container has an opening on its bottom and is placed on the sample container with the sample in the sample container before the sample is removed from the sample container.

26. The method according to claim 20, wherein a container wall of the protective container is heated in order to prevent condensation on the container wall.

27. The method according to claim 20, wherein the sample in the protective container is irradiated with UV light for sterilization.

28. The method according to claim 20, wherein the protective gas is substantially sterile.

* * * * *